US010441959B2

(12) United States Patent
Sherman et al.

(10) Patent No.: US 10,441,959 B2
(45) Date of Patent: Oct. 15, 2019

(54) MULTI-ORIFICE SPRAY HEAD (75) Inventors: Ethan G. Sherman, Jacksonville, FL (US); David J. Little, Ponte Vedra, FL (US); Wei Chen, St. Johns, FL (US); John R. Prisco, Jacksonville, FL (US); Matthew J. Friend, St. Augustine, FL (US); Matthew F. Myntti, St. Augustine, FL (US); Tom Zelmer, Raleigh, NC (US); Cyan Godfrey, Chapel Hill, NC (US); Roy Attride, Raleigh, NC (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 0 days.

(21) Appl. No.: 13/284,421

(22) Filed: Oct. 28, 2011

(65) Prior Publication Data
US 2013/0110158 A1 May 2, 2013

(51) Int. Cl.
| *A61B 17/03* | (2006.01) |
| *B05B 1/02* | (2006.01) |
| *B05B 1/14* | (2006.01) |
| *A61M 11/08* | (2006.01) |
| *B05B 11/02* | (2006.01) |
| *B05B 11/00* | (2006.01) |
| *A61M 11/00* | (2006.01) |

(52) U.S. Cl.
CPC ............ *B05B 1/14* (2013.01); *A61M 11/007* (2014.02); *A61M 11/08* (2013.01); *B05B 11/0078* (2013.01); *B05B 11/02* (2013.01)

(58) Field of Classification Search
CPC .. A61M 11/007; A61M 11/006; A61M 11/06; A61M 11/065; A61M 11/08; A61M 25/1027; A61M 25/1029; A61B 17/00491; A61B 2017/00522
USPC ............... 604/93.01, 514–517; 239/559, 567
See application file for complete search history.

(56) References Cited

U.S. PATENT DOCUMENTS

| 1,906,991 | A | 5/1933 | McTernan |
| 4,700,894 | A | 10/1987 | Grzych |
| 4,735,616 | A | 4/1988 | Eibl et al. |
| 4,923,448 | A * | 5/1990 | Ennis, III ................ A61M 5/31 128/200.14 |
| 4,950,231 | A * | 8/1990 | Liu ................................ 604/39 |
| 5,290,259 | A | 3/1994 | Fischer et al. |
| 5,464,396 | A | 11/1995 | Barta et al. |

(Continued)

FOREIGN PATENT DOCUMENTS

| CN | 1282260 | 1/2001 |
| DE | 3108918 A1 | 9/1982 |

(Continued)

OTHER PUBLICATIONS

Wolfe Tory Medical, Inc. Brochure, "It's MADgic Laryngo-Tracheal Mucosal Atomization Device", downloaded and printed from the Internet on Apr. 27, 2011.

(Continued)

*Primary Examiner* — Bhisma Mehta
*Assistant Examiner* — William R Frehe
(74) *Attorney, Agent, or Firm* — Patterson Thuente Pedersen, P.A.

(57) ABSTRACT

A spray head having multiple openings arranged to provide at spray coverage throughout at least 90 degrees from the spray head central axis. The spray head may be used for applying tissue sealants.

12 Claims, 6 Drawing Sheets

(56) References Cited

U.S. PATENT DOCUMENTS

| | | | |
|---|---|---|---|
| 5,582,596 A | 12/1996 | Fukunaga et al. | |
| 5,788,667 A | 8/1998 | Stoller | |
| 6,076,520 A * | 6/2000 | Cooper | A61M 16/0063 |
| | | | 128/200.14 |
| 6,112,743 A | 9/2000 | Denton | |
| 6,234,994 B1 | 5/2001 | Zinger | |
| 6,319,248 B1 * | 11/2001 | Nahon | A61B 18/0218 |
| | | | 604/523 |
| 6,322,542 B1 * | 11/2001 | Nilson | A61M 31/00 |
| | | | 604/257 |
| 6,471,670 B1 | 10/2002 | Enrenfels et al. | |
| 6,589,216 B1 * | 7/2003 | Abbott | A61M 3/0279 |
| | | | 604/257 |
| 6,926,711 B2 | 8/2005 | Lentz et al. | |
| 6,936,033 B2 | 8/2005 | McIntosh et al. | |
| 6,976,979 B2 | 12/2005 | Lawrence et al. | |
| 7,322,956 B2 | 1/2008 | Fehr et al. | |
| 7,455,248 B2 | 11/2008 | Kablik et al. | |
| 7,635,343 B2 | 12/2009 | McIntosh et al. | |
| 7,637,901 B2 | 12/2009 | Lawrence et al. | |
| 2002/0032463 A1 | 3/2002 | Cruise et al. | |
| 2002/0055723 A1 * | 5/2002 | Liu | A61M 3/0262 |
| | | | 604/279 |
| 2002/0177840 A1 | 11/2002 | Farnholtz | |
| 2003/0028210 A1 * | 2/2003 | Boyle | A61F 2/82 |
| | | | 606/192 |
| 2004/0059283 A1 | 3/2004 | Kirwan et al. | |
| 2004/0087932 A1 | 5/2004 | Lawrence et al. | |
| 2005/0096588 A1 | 5/2005 | Hagmann et al. | |
| 2005/0119609 A1 | 6/2005 | McLean | |
| 2006/0020256 A1 | 1/2006 | Bell et al. | |
| 2006/0219735 A1 * | 10/2006 | Faye | B01J 4/002 |
| | | | 222/71 |
| 2006/0253082 A1 | 11/2006 | McIntosh et al. | |
| 2006/0276552 A1 * | 12/2006 | Barbut | A61F 7/12 |
| | | | 514/743 |
| 2007/0005020 A1 | 1/2007 | Laveault | |
| 2008/0183128 A1 | 7/2008 | Morriss et al. | |
| 2008/0230053 A1 * | 9/2008 | Kraft | A61M 11/06 |
| | | | 128/200.23 |
| 2008/0249483 A1 | 10/2008 | Slenker et al. | |
| 2009/0076459 A1 | 3/2009 | Goldberg | |
| 2009/0108091 A1 * | 4/2009 | Steffen | A61B 17/00491 |
| | | | 239/11 |
| 2009/0198216 A1 * | 8/2009 | Muni | A61B 17/24 |
| | | | 604/514 |
| 2009/0209916 A1 | 8/2009 | Peindl et al. | |
| 2009/0269417 A1 * | 10/2009 | Gonzalez | A61K 9/0019 |
| | | | 424/616 |
| 2009/0270346 A1 | 10/2009 | Tijsma et al. | |
| 2009/0291912 A1 | 11/2009 | Tijsma et al. | |
| 2010/0072303 A1 | 3/2010 | Hayakawa | |
| 2010/0298642 A1 | 11/2010 | Trusty et al. | |
| 2011/0092892 A1 | 4/2011 | Nitsan et al. | |
| 2011/0152838 A1 * | 6/2011 | Xia | A61M 11/06 |
| | | | 604/514 |
| 2013/0066297 A1 * | 3/2013 | Shtul et al. | 604/514 |

FOREIGN PATENT DOCUMENTS

| | | |
|---|---|---|
| EP | 0363519 A1 | 4/1990 |
| EP | 2145599 A1 | 1/2010 |
| JP | SHO 50-38396 | 4/1975 |
| JP | SHO 64-19447 | 1/1989 |
| JP | HEI 8-19619 | 1/1996 |
| JP | 2003-38646 | 2/2003 |
| JP | 2006-326064 | 12/2006 |
| JP | 2011518584 | 6/2011 |
| WO | 9619940 A1 | 7/1996 |
| WO | 9932185 A1 | 7/1999 |
| WO | WO9932185 | 7/1999 |
| WO | 0071016 A1 | 11/2000 |
| WO | 0167961 A1 | 9/2001 |
| WO | 2004041424 A1 | 5/2004 |
| WO | 2005094665 A2 | 10/2005 |
| WO | 2008057802 A2 | 5/2008 |
| WO | 2009124407 A1 | 10/2009 |
| WO | WO 2009/132226 A1 | 10/2009 |
| WO | WO 2009/132228 A1 | 10/2009 |
| WO | WO2009125387 | 10/2009 |
| WO | 2010009563 A1 | 1/2010 |
| WO | 2010091527 A1 | 8/2010 |

OTHER PUBLICATIONS

Australian Examination Report No. 2 for AU Application No. 2012328596 dated Jul. 24, 2017.

European Communication for EP Application No. 12791336.6 dated Jul. 4, 2017.

Chinese Office Action for Chinese Application No. 201280052691.9 dated Aug. 9, 2017.

Japanese Notification of Reasons for Refusal for Japanese Application No. 2014539048 dated Jul. 13, 2017. English translation provided.

Chinese Decision on Rejection for Chinese Application No. 201280052691.9 dated Mar. 6, 2018. English translation not available.

Xu et al., "New Medicine Manual", Edition 3. Henan Science and Technology Publication. Feb. 28, 2005. p. 1269. English translation not available.

Japanese Decision to Grant a Patent for Japanese Application No. 2014539048 dated Jan. 17, 2018. English translation provided.

* cited by examiner

100% coverage     83% coverage     83% coverage

MULTI-ORIFICE SPRAY HEAD

TECHNICAL FIELD

The invention relates to a multi-opening spray head.

BACKGROUND

Sinusitis, an inflammation of the mucosal tissue lining the sinus walls, may lead to nasal passageway blockage, mucous stagnation and bacterial or fungal sinus cavity infection. When antibiotics cannot relieve sinusitis, sinus surgery, which involves sinus opening and mucosal tissue removal, may be an alternative. But the post-operative care for such surgery requires temporary and uncomfortable sinus packing such as lengthy gauze to support the re-opened sinus passage and to absorb excess fluid while the tissues heal. At a later time, the gauze packing has to be removed, and this removal is painful.

Sinus sealants and other biological materials have emerged as a promising technique to temporarily seal or otherwise protect the post-operative passageways with less intrusion and pain than that caused by gauze packing.

SUMMARY OF THE INVENTION

Tissue sealant application can be applied to many anatomic locations and structures. Spray application may be used to apply some sealants. Current spray head designs, however, do a poor job of coating or evenly coating some parts of the sinus cavities. An improved spray head could provide large, even spray coverage with reduced need to maneuver within sinus cavities.

The invention provides, in one aspect, a spray head comprising at least one fluid inlet and a plurality of fluid outlet openings configured to provide a substantially hemispherical or suprahemispherical spray coverage pattern.

The invention provides, in another aspect, a method of dispensing fluids on to a target body cavity site, the method comprising spraying the fluid from a spray head comprising at least one fluid inlet and a plurality of fluid outlet openings configured to provide a hemispherical or suprahemispherical spray coverage pattern.

The disclosed apparatus and method have particular use for accessing various anatomical locations such as sinus cavities and for applying tissue sealants at these anatomical locations.

BRIEF DESCRIPTION OF THE DRAWING

Like reference symbols in the various figures of the drawing indicate like elements. The elements in the drawing are not to scale.

DETAILED DESCRIPTION

The recitation of a numerical range using endpoints includes all numbers subsumed within that range (e.g., 1 to 5 includes 1, 1.5, 2, 2.75, 3, 3.80, 4, 5, etc.).

Figure 1:
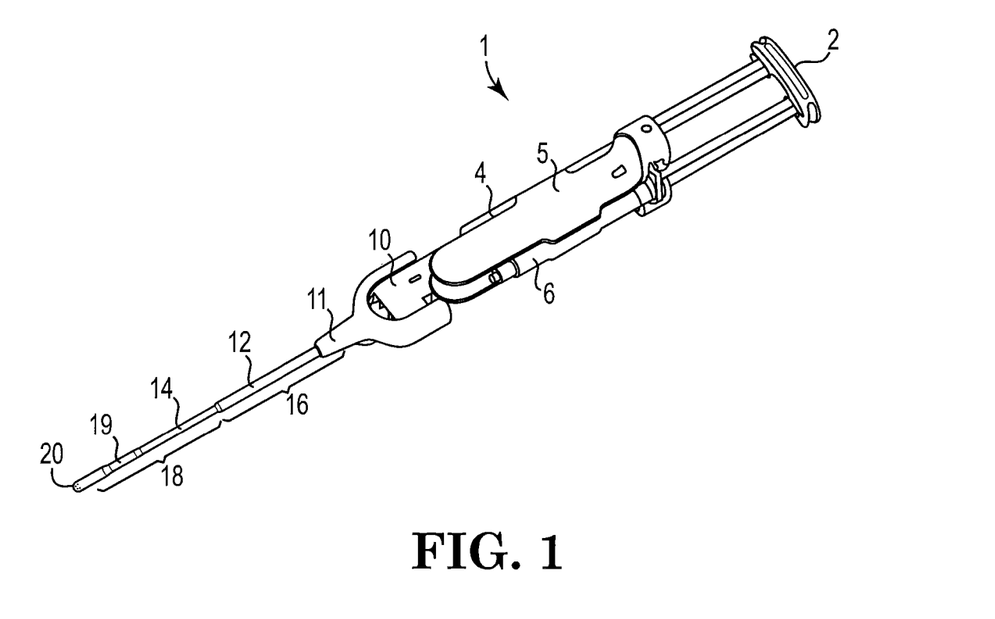
FIG. 1 is a perspective view of a spray head assembled onto a spray delivery system.

The present invention provides, in one aspect, a spray head and, in other aspects, a method of delivering tissue sealants using such spray head. FIG. 1, which shows an exemplary spray delivery system 1, in general, includes an actuating member 2, body 5 capable of receiving delivery devices (which in FIG. 1 are syringes 4, 6), a manifold 10 surrounded by a shroud 11, a support member 12, a cannula 14 which may be constrained at the proximal end portion 16 providing rigidity, and unconstrained at the distal end portion 18 providing flexibility, a sheath 19, and a spray head 20. The cannula 14 and spray head 20 are connected to body 5 through manifold 10. The manifold 10 engages body 5 and is connected to syringes 4, 6, and aids in dispensing fluid components stored in syringes 4, 6.

The spray head 20 is designed to include multiple openings at various angles and at various locations to enable material(s) entering the spray head 20 to exit in multiple directions. The spray head 20 may, for example, be used in a multi-component spray delivery system with a multi-lumen or multi-sectioned cannula as shown in FIG. 1 and as described in detail in U.S. patent application Ser. No. 13/284,600 and in U.S. patent application Ser. No. 13/284,387 (now U.S. Pat. No. 8,974,436 B2), respectively, both filed Oct. 28, 2011 and each of which is incorporated herein by reference in its entirety.

The spray head 20 may be used to apply compositions containing a variety of agents, such as multiple-component tissue sealant compositions, to a variety of bodily passageways or cavities including the nasal cavity (maxillary, frontal and sphenoid sinuses). Exemplary multi-component tissue sealants may include crosslinkable polysaccharide systems, for example, a first component containing chitosan or a chitosan derivative and a second component containing starch or a starch derivative. Other exemplary multi-component tissue sealants are provided in U.S. patent application Ser. No. 12/429,141, now published as U.S. Publication No. 2009/0270346 and U.S. patent application Ser. No. 12/429,150, now published as U.S. Publication No. 2009/0291912.

Figure 2:
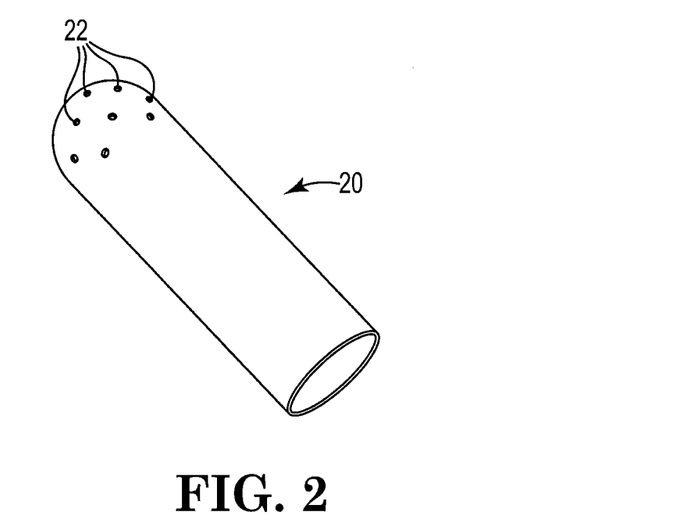
FIG. 2 is a perspective view of an exemplary spray head.
Figure 3:
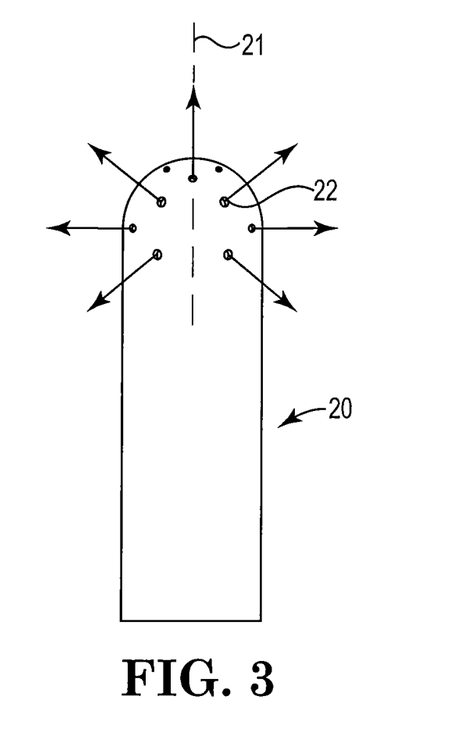
FIG. 3 is a plan view of the spray head of FIG. 2.

As shown in FIGS. 2 and 3, spray head 20 has multiple fluid spray outlet openings 22 at a variety of angles and at locations to permit fluid material(s) to exit in multiple directions. Although the distal end of spray head 20 may have a variety of shapes, spray head 20 desirably has a hemispherical shape with openings 22 desirably being arranged to provide a substantially hemispherical or suprahemispherical, substantially uniform spray pattern.

Depending on the spray coverage required, other opening arrangements beyond those shown in FIG. 2 are possible on spray head 20. The spray head 20 may have, for example, at least 10, at least 12, or at least 14 outlet openings and up to 32, up to 28 or up to 26 openings distributed at various planes separated by a distance of about 0.025 cm, 0.05 cm, or 0.075 cm over the distal end of spray head 20. This arrangement provides a larger spray coverage area as opposed to spray coverage from a single orifice or from orifices arranged in a single plane and minimizes a need to rotate or manipulate the spray head 20 once inserted into a passageway. The spray head openings 22 allow for spray coverage patterns over, for example, an arc extending at least 90 degrees, at least 135 degrees, or at least about 150 degrees from a central axis 21, as shown in FIG. 3.

Figure 4:
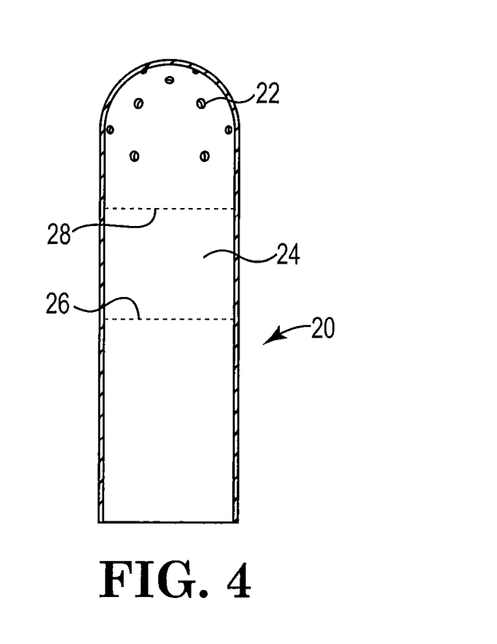
FIG. 4 is a cross sectional view of the spray head of FIG. 3.

FIG. 4 shows a cross sectional view of the spray head 20 with a space or region 24 as defined by 26, which defines the end of a lumen inserted in tip 20; and 28, which defines the distal end of space or region 24 which permits fluids exiting the lumen to mix before exiting spray head 20. The space or region 24, the mixing area may be, for example, from about 0.02 cm to 1.5 cm.

Spray head 20 may be made from a variety of materials, for example, stainless steel or other medically acceptable metal or alloy. Other materials suitable for spray head 20 include polyvinyl chloride (PVC), nylon, polyether ether ketone (PEEK), acrylonitrile butadiene styrene (ABS) and the like.

The spray head 20 desirably has a length enabling easy insertion and withdrawal of spray head 20 into an anatomical location. For example, for use in sinus cavities the spray head length preferably is about 5.0 mm to 20 mm, spray head wall thickness preferably is about 0.01 mm to 1.0 mm, more preferably about 0.2 mm; the spray head opening diameters preferably are about 0.01 mm to 3.0 mm, and the spray head outer diameter preferably is about 0.5 mm to 10 mm, more preferably 3-5 mm. The openings may, for example, be circular, round, oval or semi-circular in shape. The angle of the openings with respect to the spray head central axis 21 preferably is, for example, from about 0, 45, 90 and 120 degrees.

Cannula 14 may be a flexible or malleable member that may be assembled to include a rigid proximal end portion 16 and a malleable distal end portion 18. The rigid proximal end portion 16 may be constrained at the proximal end by support shaft 12 and shroud 11, which prevents or discourages cannula bending. The rigid proximal end portion 16 also includes the portion of cannula 14 surrounded by the support shaft 12. Cannula 14 may be bent at the malleable distal end portion 18, which extends from the end of the support shaft 12 up to the proximal portion of the spray head 20.

Cannula 14 and spray head 20 are connected to body 5 through manifold 10. Manifold 10 may be surrounded by a shroud 11 with support shaft 12 constraining the proximal end of cannula 14. Manifold 10 may be configured to receive portions of syringes 4, 6 without requiring threaded or rotating engagement of the syringe to manifold 10 to provide a liquid tight connection. Spray head 20 is connected to malleable distal end portion 18. Covering the interface between the malleable distal end portion 18 and spray head 20 is a sheath 19 which provides a smooth transitional interface at the joint between cannula 14 and spray head 20.

When used to deliver a tissue sealant to a sinus cavity, cannula 14 preferably has an overall length of about 10 cm to 15 cm, more preferably about 12 to 13 cm. The rigid proximal end portion 16 may have a length, in the range from about 4 cm to 8 cm, preferably about 5 cm to 7 cm, and the malleable distal end portion 18 may have a length, for example, in the range from about 4 cm to 8 cm, preferably about 5 cm to 7 cm. The outer diameter of cannula 14 may be from about 0.1 cm to 1.0 cm, preferably about 0.3 cm to 0.4 cm. The ratio of the rigid proximal end portion 16 to the malleable distal end portion 18 may be in a ratio of about 2:1 or about 1:2, and preferably about 1:1.

Depending on the specific cannula use, other dimensions are also acceptable. For example, cannula 14 may be used in laparoscopic anatomical or gynecological surgery, neural surgery, pulmonary surgery or the like.

The cannula 14 may be formed of a material acceptable for use inside the human body and of a selected durometer (hardness). The selected durometer aids in preventing the cannula from kinking when bent greater than 45 degrees, greater than 90 degrees or greater than 180 degrees with respect to a straight, unbent configuration. The selected material may include for example, thermoplastic or thermoset polymers such as polyolefins, silicones, polyvinyl chlorides, polyurethanes, polyesters and the like. To attain a desired durometer, fillers or plasticizers may be used. The amount and type of filler or plasticizer is determined by the selected thermoplastic or thermoset polymers used. Cannula 14 may have a durometer (Shore A) in the range, for example, from 60 to 95, preferably from about 85 to 95.

Referring to FIG. 2, support member 12 may be in the form of a cylindrical metal or plastic tube surrounding cannula 14 and molded within or otherwise connected to the distal end portion of shroud 11, for example, by adhesive or welding. The support member 12 preferably is made of stainless steel. Other exemplary materials include, for example, metals such aluminum and plastics such as thermoplastic or thermoset polymers. The support member 12 desirably has a thickness and length such that it minimizes physical obstruction during anatomic insertion and resists sideways deflection of proximal end portion 16 so as to provide improved control when maneuvering and navigating cannula 14 through bodily passageways. The support member 12 may, for example, have a thickness of about 0.01 cm to about 0.1 cm, preferably from about 0.02 cm to 0.03 cm; and a length, for example, of about 3 cm to 10 cm, preferably from about 4.5 cm to 5.5 cm.

Figure 6:
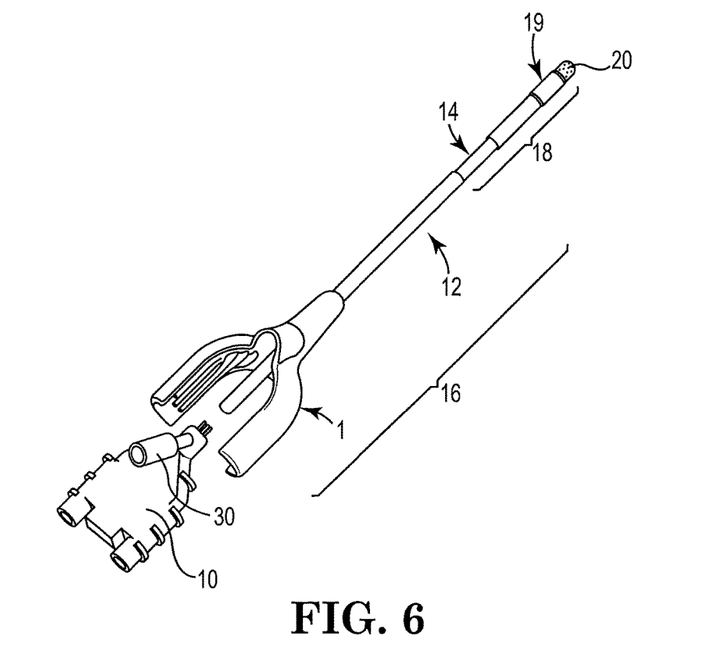
FIG. 6 is a perspective, exploded view of the spray delivery system of FIG. 1.

As illustrated in FIG. 1 and FIG. 6, shroud or casing 11 surrounds outer portions of manifold 10. The shroud 11 also engages the support member 12, and when assembled to cannula 14, provides additional proximal rigidity to the cannula 14. Shroud 11 may be permanently attached to the manifold 10, for example, by adhesives, welding or injection molding or may be optionally removable.

Figure 7A:
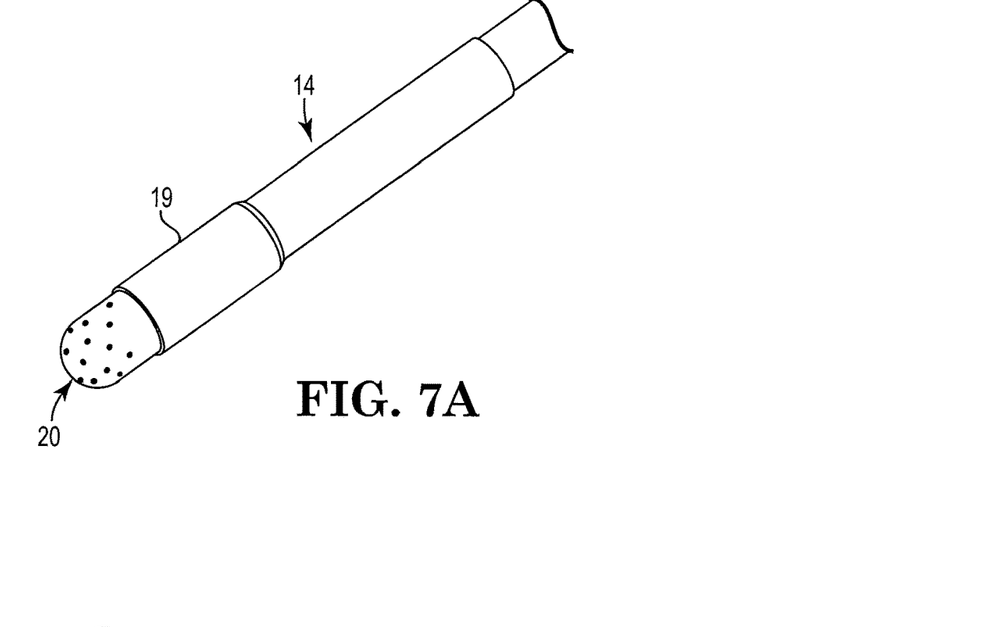
FIG. 7A is a perspective view of a distal portion of a cannula.
Figure 7B:
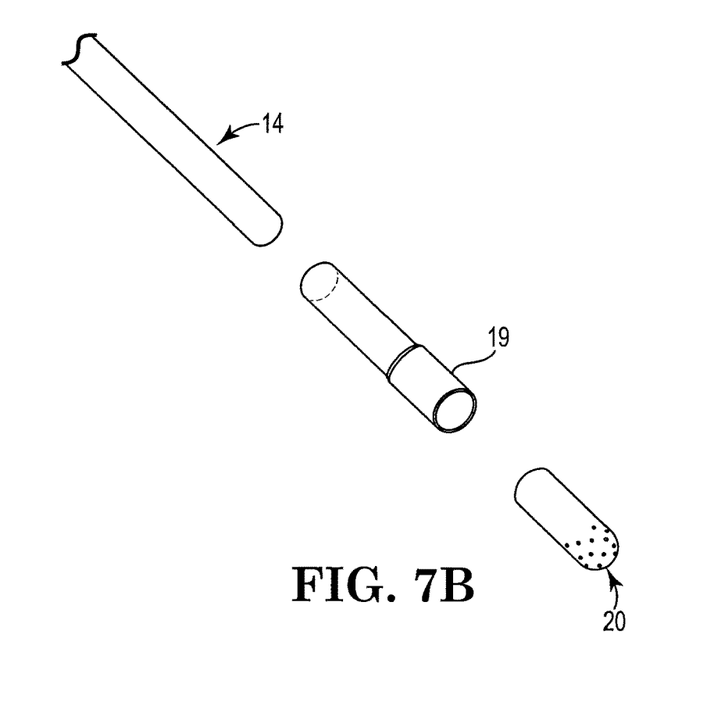
FIG. 7B is a perspective, exploded view of components in FIG. 7A.
Figure 7C:
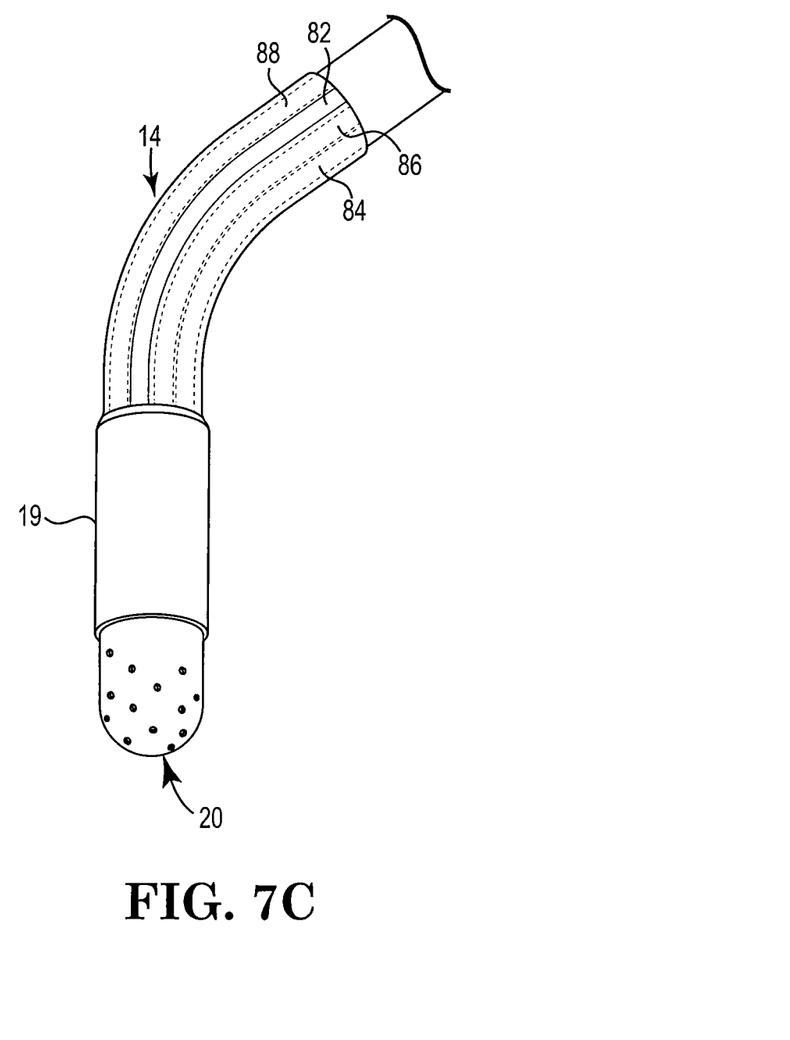
FIG. 7C is a perspective view of the FIG. 7A components after cannula 14 has been bent to a new shape.

As illustrated in FIG. 7A and FIG. 7B, sheath 19 may, for example, surround the proximal portion of spray head 20 and the distal end portion 18 producing a smooth interface between the spray head 20 and cannula 14. Sheath 19 also helps keep spray head 20 firmly attached to cannula 14 when withdrawing spray head 20 from a confined location.

Desirable lengths of sheath 19 may for example, range from about 10 mm to 50 mm, preferably from about 20 mm to 25 mm. A thickness for sheath 19 desirably may be selected such that it minimizes interference with anatomical features during cannula insertion. The sheath thickness may, for example, range from to 0.001 cm to 0.010 cm, preferably 0.001 cm to 0.003 cm. The sheath 19 may be a heat shrink tube, a mechanically expanded tube, or an extruded plastic tube, and may be made from a variety of materials, for example, polyester, polyolefin, and fluoropolymers.

Figure 8A:
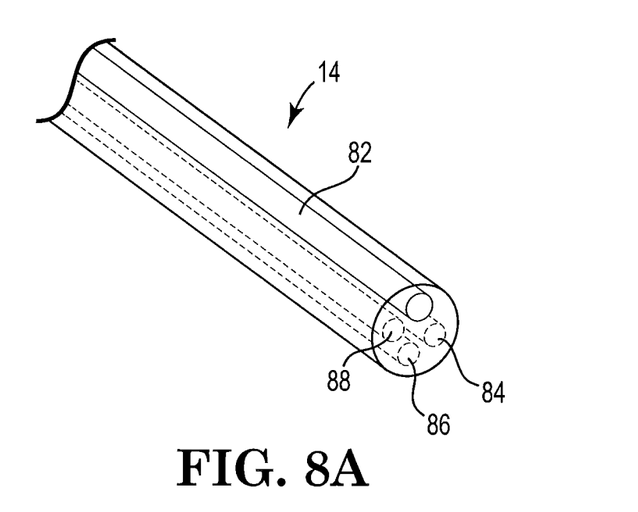
FIGS. 8A and 8B are perspective views, partially in phantom, of cannula 14 from FIG. 7A and FIG. 7B.
Figure 8B:
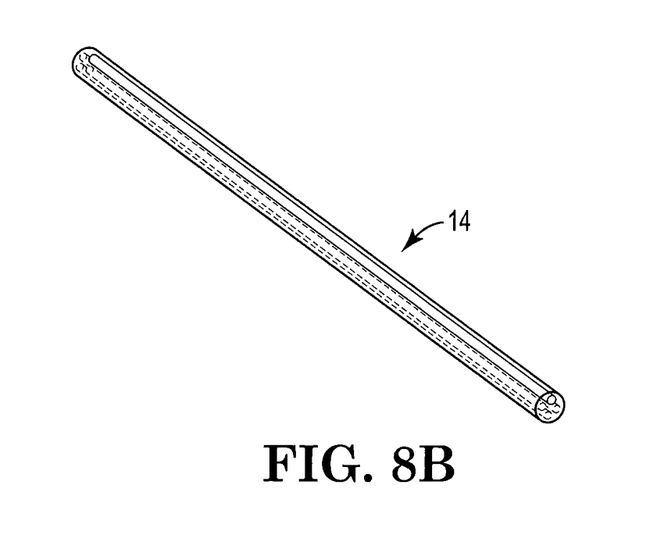

As shown in FIG. 8A and FIG. 8B, an exemplary cannula 14 may enclose multiple lumens that extend the entire cannula length, from the rigid proximal end portion 16 to the malleable distal end portion 18 and maintains the separation of each lumen. The individual lumen diameters are dependent on a number of factors, including the spray head opening diameters, the desired pressure and flow rate. The lumens may, for example, all be of the same diameter and cross sectional shape. The lumen shape may be, for example, circular, oval, square or D-shaped in cross-section, with the flat portions of neighboring D-shapes being adjacent to one another.

As illustrated in FIG. 8A, at least one of the lumens may include a reinforcement member 82 to allow selective bending of the cannula 14 to fit different orientations. The reinforcement member 82 may, for example, be in the form of a wire located within and extending along the length of a lumen. The reinforcement member 82 may, but need not be centrally located in the multi-lumen cannula 14. In such embodiments, the cannula 14 may be formed with at least two lumens, one of which will become occupied by the reinforcement member 82. The cannula 14 may also be formed by extruding or molding it over the reinforcement member 82 and by providing at least one lumen through which fluid may flow.

The reinforcement member 82 may be made of, for example, metal or a metal alloy such as stainless steel, copper, aluminum or the like. In other examples, reinforcement member 82 may be made of a shape memory metal such as Nitinol. The diameter of the reinforcement member 82, may, for example, range from 0.001 cm to 0.10 cm, preferably 0.03 cm to 0.05 cm. The shape of the reinforcement member 82 may be, for example, circular, oval, square or D-shaped in cross-section. The stiffness of the reinforcement member 82 may be full hard, half hard, quarter hard, annealed, soft or any other desired stiffness depending on the desired application.

The cannula 14, illustrated in FIG. 8A and FIG. 8B, includes four lumens, one of which is occupied by reinforcement member 82. Remaining lumens 84, 86, 88 are in fluid communication with one or more fluid supplies such as syringes 4, 6 and a source of pressurized air (not shown) that may be introduced into lumen 88 via port 30, which is shown in FIG. 6.

In one exemplary assembly process for the disclosed device, an operator first inserts the actuating member 2 into body 5. Alternatively, actuating member 2 may be preassembled with body 5. Syringes 4, 6 are positioned against body 5 and actuating member 2 so that body 5 and actuating member 2 can receive and capture syringes 4, 6. In this manner, syringes 4, 6 are held substantially parallel in body 5.

Once the syringes are received and captured by body 5, cannula 14 and spray head 20 are assembled to body 5 through manifold 10. Cannula 14 and spray head 20 may if desired be preassembled to manifold 10 during manufacturing.

The operator then connects manifold 10 to syringe outlets to provide an unthreaded, liquid-tight connection such that the syringe contents in syringe barrels are in fluid communication with cannula 14 through manifold 10.

When the delivery device 1 is fully assembled, the operator shapes the cannula 14 to a desired shape. Cannula 14 desirably is sufficiently stiff so that it will retain its shape until bent into a new shape. The shaped cannula 14 and spray head 20 are then maneuvered or navigated into a desired treatment site within the patient's body, for example, a nasal or sinus cavity or other opening, recess or passageway. Once satisfactorily positioned, an operator may, for example, depress actuating member 2 to move the plunger of syringe 4, 6 toward the syringe outlets, advancing the fluid syringe contents substantially at the same time through the separate syringe barrels and out into respective fluid channels in manifold 10 which maintain the fluid separation. Continued force will advance the fluids through the multi-lumen cannula 14 and into a region within spray head 20 where they mix before the mixed fluids exit spray head 20. If compressed gas is used, it may be supplied through port 30. The gas stream passes through a lumen of multi-lumen cannula 14 into the mixing region of spray head 20. The gas stream helps atomize the mixed syringe contents resulting in much smaller droplets. Overall, a smoother manipulation and easier control of the device through passageways is provided.

The invention is further illustrated in the following non-limiting examples.

Example 1

A spray head like that shown in FIGS. 2 and 3 was prepared with an outer diameter of 4 mm and having 26 openings. The openings were arranged at 5 different planes and five different angles along the length of the spray head hemisphere. The first set of 4 openings on the first plane (starting from the distal end) was 30 degrees from the central axis. The second set of 4 openings on the second plane was 45 degrees from the central axis. The third set of 6 openings on the third plane was 67.5 degrees from the central axis. And the fourth and fifth sets of 6 openings on the fourth and fifth plane each were 90 degrees from the central axis. All openings were symmetrically located along the diameter of the spray head. The diameter for all 26 openings was 0.0254 cm. The wall thickness of the spray head was 0.0254 cm. The spray head was assembled onto a delivery device and the spray coverage was measured as follows. A 1.5 cm (0.6 inches) portion of the spray head was inserted into the center of a uniform spherical plastic test chamber and approximately 2 ml total (1.0 ml per syringe) of a mixture of carboxymethyl chitosan and starch was sprayed into the test chamber by depressing the plunger in a steady motion. A 50 psi air source was supplied to the spray head to assist in biomaterial delivery. The sprayed material was allowed to crosslink for one minute after which the spherical test chamber was opened and the gel coverage area on the top half of the sphere was observed and recorded.

Figure 5:
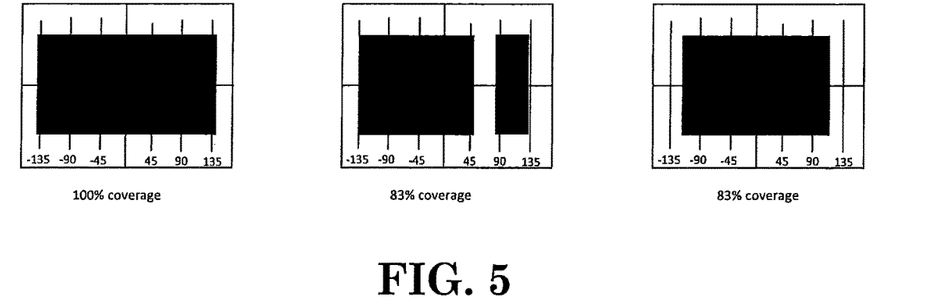
FIG. 5 shows gel coverage maps obtained using the spray head of FIG. 2.

Examples of spray coverage data are shown in FIG. 5. The coverage maps are representative of spherical test data laid out on a 2D flat surface like a map with the central (0,0) point indicating the central spray head location. The black regions indicate complete gel coverage and the white regions (gaps) indicate no gel coverage. A 100% coverage rating was taken to be coverage over at least a 270° arc, or coverage over at least a 135° arc on either side of central axis 21.

Example 2

Using the experimental set up described in Example 1, gel thickness was also measured. Using a 3 mm wide blade, portions of the crosslinked gel on the top half of the sphere were scraped to create a "test area" or "valley." Using a Keyence microscope the gel thickness was determined on either side of the test area and recorded as shown below.

Each test was conducted five times. Two measurements were taken per test one from the left and one from the right side of the test area.

TABLE 1

| Gel Coverage Area Thickness Variability Measure | | |
|---|---|---|
| Experiment # | L-Side Thickness (in) | R-Side Thickness (in) |
| 1 | 0.0083 | 0.0063 |
| 2 | 0.0084 | 0.006 |

TABLE 1-continued

Gel Coverage Area Thickness Variability Measure

| Experiment # | L-Side Thickness (in) | R-Side Thickness (in) |
|---|---|---|
| 3 | 0.009 | 0.0086 |
| 4 | 0.0066 | 0.0070 |
| 5 | 0.0054 | 0.0071 |
|   | 0.0075 ± 0.0015 | 0.007 0.001 |

The gel coverage on either side of the test area showed a difference of 0.0005 inches (<10%). In other words, the gel thickness showed only a 2 fold difference from one side to the other side of the test area, indicating consistent, uniform gel coverage.

We claim:

1. A method of dispensing fluids to a target body cavity site in a sinus cavity, the method comprising:
inserting into the sinus cavity a spray head comprising at least a fluid inlet and a plurality of fluid outlet openings configured to provide at least a hemispherical spray coverage pattern, wherein the spray head has a length of about 5.0 to 20 mm, is connected to a flexible multi-lumen cannula, and defines a mixing space or region where fluids exiting lumens of the flexible multi-lumen cannula mix before exiting the spray head, and
spraying the fluids through the spray head, including supplying pressurized air through a gas lumen in the flexible multi-lumen cannula, and wherein the pressurized air mixes with the fluids in the mixing space or region in the spray head to assist in spraying the fluids;
withdrawing the spray head from the sinus cavity with the flexible multi-lumen cannula extending out of the target body cavity site attached to the spray head.

2. The method of claim 1 comprising spraying a tissue sealant.

3. The method of claim 1 comprising spraying a mixture of chitosan and starch.

4. The method of claim 1 wherein the spray head provides a suprahemispherical spray coverage pattern.

5. The method of claim 1 wherein the spray head provides a spray coverage pattern extending over at least about a 90 degree arc on either side of a central axis.

6. The method of claim 1 wherein the spray head has 20 to 30 fluid outlet openings.

7. The method of claim 1 wherein the spray head is made of stainless steel.

8. The method of claim 1 wherein the spray head has an outer diameter of about 0.5 to about 10 mm.

9. The method of claim 1 wherein the spray head has a wall thickness of about 0.01 to about 1.0 mm.

10. The method of claim 1 wherein the plurality of fluid outlet openings are arranged at angles of 30 to 90 degrees with respect to a central axis.

11. The method of claim 1 wherein the plurality of fluid outlet openings are separated by distances of about 0.025 to 0.075 cm.

12. The method of claim 1 wherein the spray head can be inserted into and withdrawn from the sinus cavity.

* * * * *